United States Patent [19]

Netznik

[11] Patent Number: 4,525,130

[45] Date of Patent: Jun. 25, 1985

[54] ADJUSTABLE MOLDING FRAME

[76] Inventor: Frederick P. Netznik, 8556 Central Park Ave., Skokie, Ill. 60076

[21] Appl. No.: 607,933

[22] Filed: May 7, 1984

[51] Int. Cl.³ .............................................. B29D 27/00
[52] U.S. Cl. ...................................... 425/2; 425/175; 425/DIG. 29; 425/DIG. 60
[58] Field of Search .............. 425/2, 175, 453, 405 R, 425/DIG. 29, DIG. 60; 249/82

[56] References Cited

U.S. PATENT DOCUMENTS

| | | | |
|---|---|---|---|
| 3,065,511 | 11/1962 | Leitzel | 425/DIG. 29 |
| 3,264,382 | 8/1966 | Augell et al. | 425/2 X |
| 3,458,898 | 8/1969 | Casparis | 425/2 |
| 3,830,896 | 8/1974 | Flicker et al. | 425/2 X |
| 4,038,014 | 7/1977 | Dusza et al. | 425/405 R X |
| 4,454,090 | 6/1984 | Saumell | 425/175 X |
| 4,470,782 | 9/1984 | Zimmerman et al. | 425/2 |

FOREIGN PATENT DOCUMENTS 976229 10/1950 France ............................. 425/2

Primary Examiner—J. Howard Flint, Jr.
Attorney, Agent, or Firm—Emrich & Dithmar

[57] ABSTRACT

A multiply adjustable frame includes coupled seat and back pans each provided with a flexible, sealed, bead-filled bag connected to a respective vacuum pump. With a person positioned on the frame, the seat and back bags assume the contour of respective portions of that person's torso and are maintained in this configuration upon evacuation by a vacuum pump. Cushions individually contoured to the person thus fitted may then be formed either directly from the evactuated bag or from a negative plaster cast of the evacuated bag. The adjustable molding frame, the configuration of which may be varied over a wide range of angles and dimensions, is particularly adapted to provide a custom bucket seat including custom contoured seat and back cushions for the severely handicapped and deformed. Seat pan length, or depth, and seat-to-back angle may be continuously varied over a wide range of values. In addition, the entire frame may be rotated rearward about a horizontal axis adjacent the intersection of the seat and back pans to position the person in a seated, inclined attitude in forming the back cushion to the contour of a rear portion of the person's torso. Adjustable foot supports are provided for proper positioning of the legs during the bucket seat fitting procedure. The frame may be secured in a locked position to retain the measured contour configuration when the person being fitted is no longer positioned on the frame.

18 Claims, 15 Drawing Figures

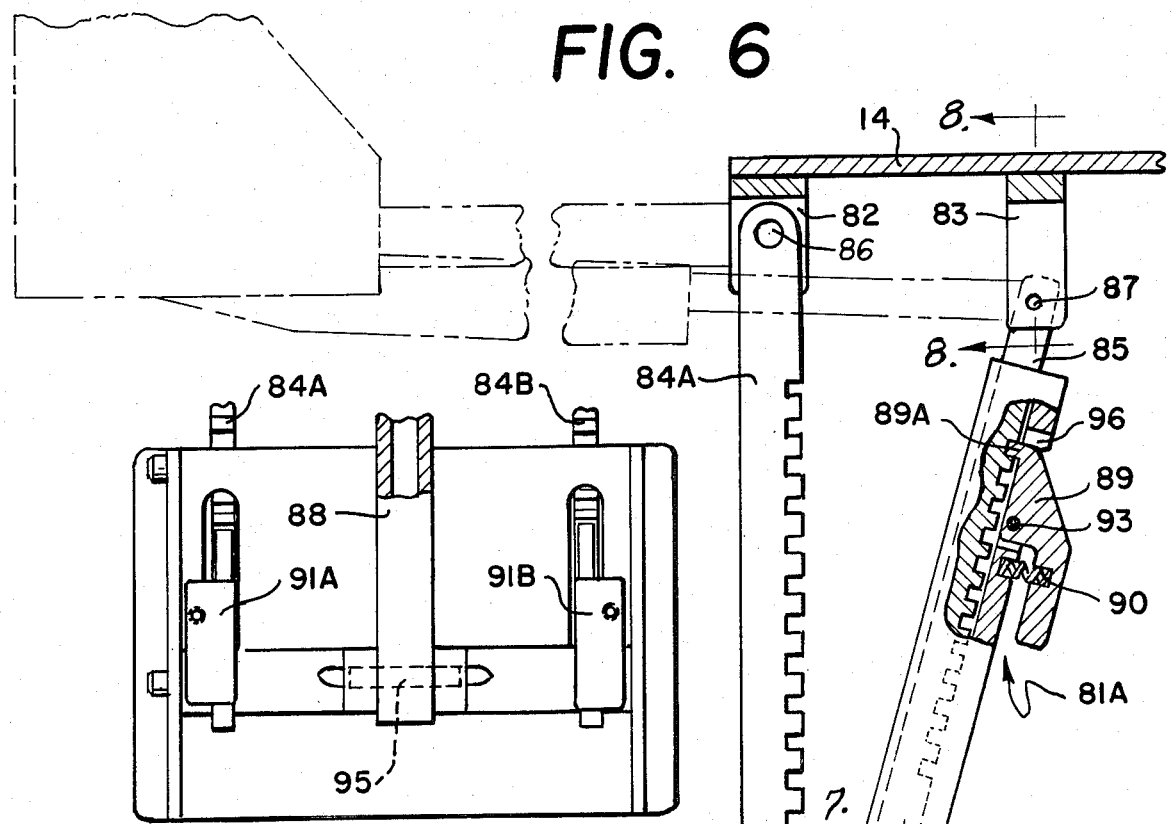
FIG. 6
FIG. 7
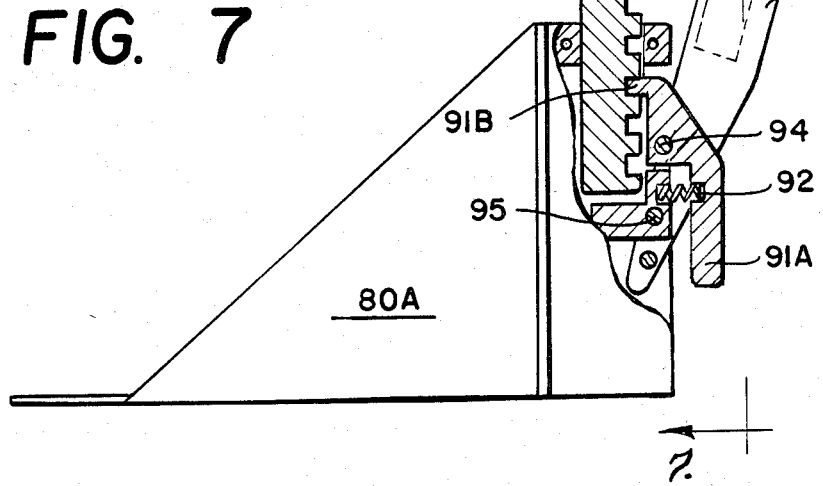
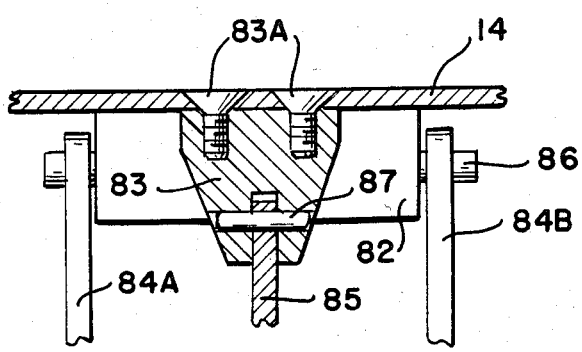
FIG. 8

ADJUSTABLE MOLDING FRAME

BACKGROUND OF THE INVENTION

This invention relates generally to a frame for supporting a person in a seated position and is particularly directed to a variably configured frame for use in forming a uniquely configured and contoured bucket seat.

For a person confined to a wheelchair the surfaces upon which his or her body is supported are particularly important. These support surfaces are not only important from a comfort standpoint, but also may be designed to provide support where necessary. In terms of providing comfort, it is important that the support surfaces maximize the area of contact with the user in distributing pressure over as large an area as possible in order to minimize the possibility of pressure sores and the discomfort associated therewith. For the more severely handicapped and deformed, some support may be provided by appropriate contouring of the seat and back support surfaces to match the body configuration of the user. The more closely the contoured surfaces correspond in a complementary manner to the seat and back portions of the user, the greater the comfort, support and stability of the user.

The first step in fabricating the aforementioned contoured support cushions involves making an impression of the person's back and seating areas. The contoured cushions may then be fabricated directly from the thus formed impressions, or may make use of an intermediate negative plaster cast of the person's surface impression in fabricating the contoured support cushions.

Prior art devices used in forming the negative impression containing the contours of the support surfaces of one's body have suffered from various limitations. For example, ideally the back and seat impressions should be made in the same sitting in order to most accurately reflect the user's configuration. However, with the seat oriented generally horizontally and the back oriented generally vertically, the deformable material in the bag-like back support enclosure tends to collect in the lower portion of the enclosure adjacent the lower back resulting in an inaccurate impression of the person's back contour. In addition, apparatus for making these contoured surface impressions have in the past been unwieldy, overly complicated and expensive, and have provided only a limited range of configurations and orientations of the various elements thereof resulting in back and seat contoured surfaces which only approximate those of the person being measured and fitted. Finally, to date, the time required to accurately take a seating surface impression as previously described has been overly extended and has substantially contributed to the discomfort of the person being measured and fitted particularly where that person is suffering from a neuromuscular disease complicated by spinal curvature.

The present invention is intended to overcome the aforementioned limitations of the prior art by providing an adjustable molding frame which may be selectively adjusted in configuration to precisely conform to the contours of the seating and support surfaces of a person positioned thereon. The various degrees of freedom in the adjustable molding frame in combination with easily adjustable controls, which may be securely locked in position once the desired configuration is achieved, permit seat and back surfaces uniquely contoured to the person being measured and fitted to be accurately formed.

OBJECTS AND SUMMARY OF THE INVENTION

Accordingly, it is an object of the present invention to provide a variably configured frame for use in fabricating a uniquely configured and contoured bucket seat.

It is another object of the present invention to provide a flexible support frame for a moldable seating surface from which seat and back support surfaces uniquely fitted to an individual may be fabricated.

Yet another object of the present invention is to provide apparatus for fabricating individually fitted seat cushions particularly adapted for use by the deformed, handicapped or infirm.

Still another object of the present invention is to provide a chair support frame having various degrees of freedom, the seat and back portions of which may be individually configured and dimensioned.

These and other objects are realized in a multiply adjustable seat support frame having a coupled seat pan and back frame arrangement and bead-filled bags associated therewith. Each bag is coupled to a respective vacuum pump for the evacuation thereof when a person is positioned on and supported by the seat and back bags. The moldable beads confined in a bag permit the surface of each bag to assume the contour of the person positioned thereon, from which an individually contoured cushion may be formed either directly or by means of a negative plaster cast as an intermediate stage. The present invention is particularly adapted for the fabrication of a bucket seat having seat and back cushions uniquely contoured and fitted to one who is deformed, handicapped or infirm.

The seat support frame includes means for adjusting the seat-to-back angle as well as the seat pan length, or depth, according to the requirements of the person being fitted. Adjustable foot supports are coupled to a forward portion of the seat pan for proper leg positioning during the fitting operation. A tilt adjustment is provided for tilting the frame rearward wherein the full weight of the person is directed against the back bag for obtaining an accurate impression of the rear portion of the person's torso. The frame may then be tilted forward and generally vertical for obtaining an accurate impression of the subject's seat and upper, rear leg areas and for facilitating the entry onto and exit from the seat support frame. Means are provided for locking the frame in a given configuration and orientation to facilitate the formation and retention of surface contour impressions of the subject's body support surfaces.

BRIEF DESCRIPTION OF THE DRAWINGS

The appended claims set forth those novel features believed characteristic of the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

FIG. 6 is a vertical plan side view of an adjustable foot support assembly for use in the adjustable molding frame of the present invention;

FIG. 7 is a sectional view taken along sight line 7—7 in FIG. 6 showing details of a rear portion of an adjustable foot support;

FIG. 8 is a sectional view taken along sight line 8—8 in FIG. 6 showing the arrangement for mounting an adjustable foot support upon a lower portion of a seat pan in the adjustable molding frame;

DETAILED DESCRIPTION OF THE PREFERRED EMBODIMENT

Figure 1:
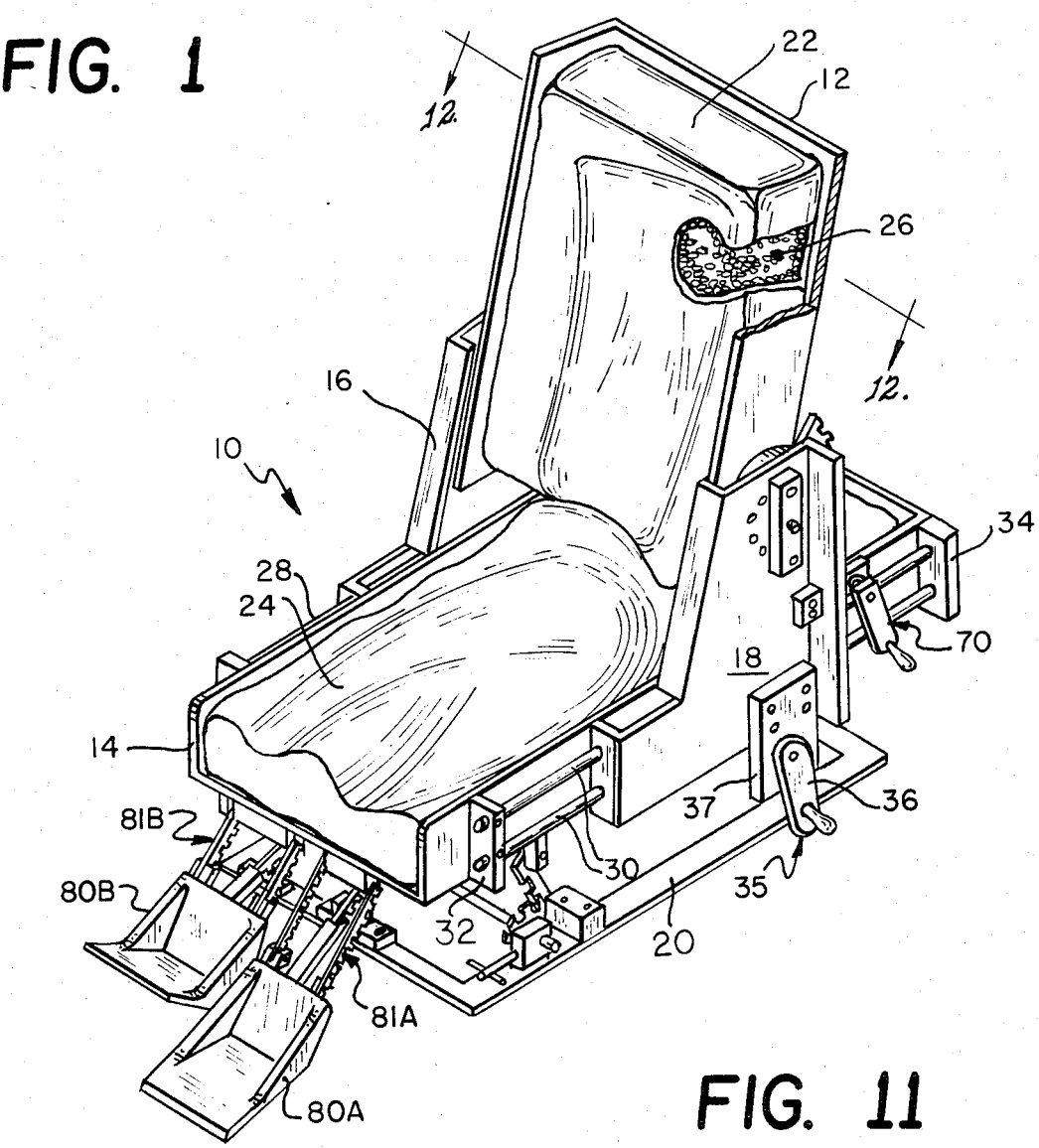
FIG. 1 is an upper perspective view of an adjustable molding frame including deformable back and seat support bags in accordance with the present invention.

Referring to FIG. 1, there is shown an upper perspective view of an adjustable molding frame 10 in accordance with the present invention.

The adjustable molding frame 10 includes a back panel 12 and a seat pan 14 which are coupled together by means of right and left generally L-shaped brackets 16, 18 and right and left seat pan guide bars 28, 30. As used hereinafter, right and left refer to respective lateral portions of the adjustable molding frame when viewed from the rear. The right and left seat pan guide bars 28, 30 are each coupled to lateral portions of the seat pan 14 by means of forward and aft mounting brackets 32, 34. The right and left coupling brackets 16, 18 may be displaced along the right and left guide bars 28, 30 by means of a seat depth control assembly 35 described in detail below. By adjustably displacing the right and left coupling brackets 16, 18 and back panel 12 coupled thereto, the length of the seat pan 14 positioned forward of the back panel 12 may be adjusted to fit the seat and upper leg dimensions of a person positioned on and supported by the adjustable molding frame 10.

The seat pan 14 is mounted to a support frame 20. A flexible back vacuum container 22 in the general form of a bag comprised of latex rubber is positioned on the back panel 12. Similarly, a flexible seat vacuum bag 24 is positioned on and supported by the seat pan 14. The back and seat vacuum bags 22, 24 each are provided with a plurality of beads 26 therein. The beads 26, which are comprised of polyethylene and are generally ovular in shape, are loosely contained within a respective vacuum bag and are free to move relative to one another therein. A fitting (not shown in FIG. 1) is provided in each of the back panel 12 and the seat pan 14 for coupling a respective sealed vacuum bag to a vacuum pump (also not shown in FIG. 1). When a vacuum bag is evacuated by means of a vacuum pump with a person positioned upon and supported by the back and seat vacuum bags 22, 24 in the adjustable molding frame 10, the surfaces of the respective vacuum bags assume the contour of corresponding seating surfaces of the person positioned thereupon. In this manner, contoured surfaces accurately representing the seating surfaces of the person positioned on the adjustable molding frame 10 may be formed.

In a typical operation, the surfaces of the back and seat vacuum bag 22, 24 may be formed generally in the shape of the person to be fitted before a vacuum is applied to either bag. A slight vacuum may then be applied in order to stabilize the configuration of the beads in each of the vacuum bags while the person is positioned on the adjustable molding frame 10. When appropriate positioning has been determined, the back and seat vacuum bags are then evacuated and the beads therein retain the contoured configuration of the person positioned thereon even after the person is removed from the adjustable molding frame. Typically, a pressure of 25 inches of Hg is used in order to preserve the bead arrangement within a vacuum bag and maintain the uniquely contoured surface thereof. In one approach, a plaster mold may then be formed from the thus contoured vacuum bag and appropriately contoured cushions may be fabricated from these molds. In another approach, the contoured cushions may be made directly from the evacuated back and seat bags 22, 24.

Coupled to a lower, forward portion of the seat pan 14 by means of respective adjustable positioning assemblies 81A, 81B are a pair of foot supports 80A, 80B which also serve as leg rests. Proper positioning of the adjustable foot supports 80A, 80B so as to support the feet and legs of a person positioned on the adjustable molding frame 10 ensures that the seat vacuum bag 24 will assume the precise contour of the seating surface, including the upper, aft leg portions, of a person positioned thereon. In forming an accurate impression of the person's seating surface, it is essential that his or her feet be supported in a normal sitting position which is accomplished by means of foot supports 80A, 80B.

Figure 2:
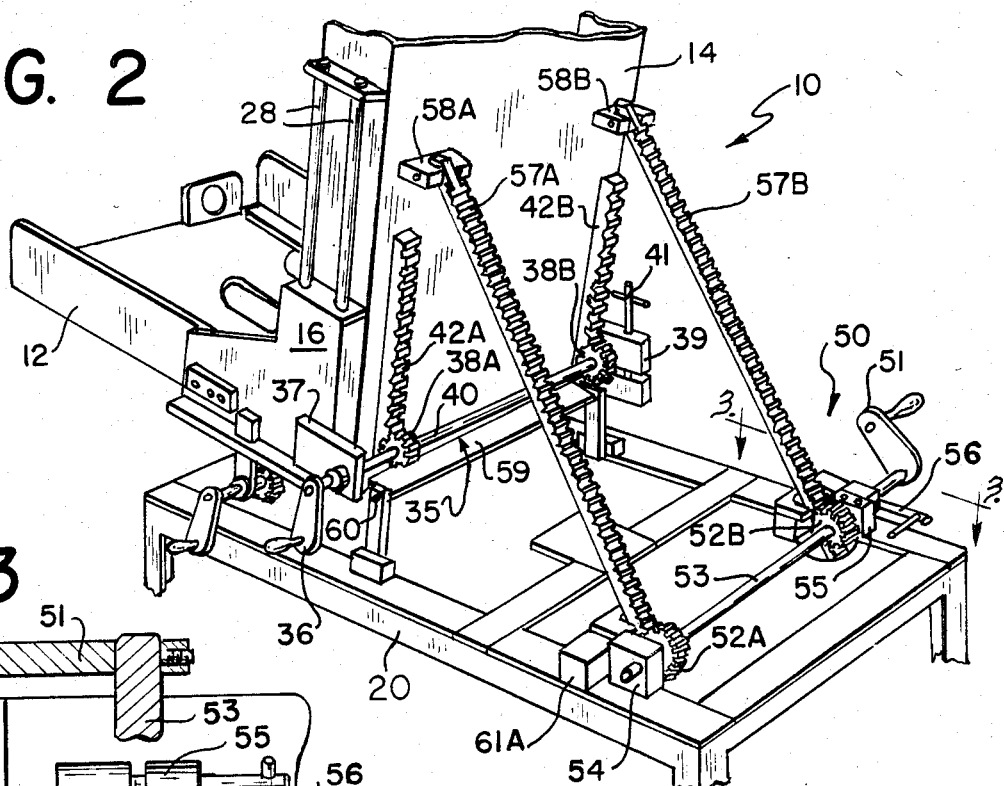
FIG. 2 is a perspective view showing the adjustable molding frame of FIG. 1 in the fully tilted back position for obtaining an impression of the contour of the rear torso area of one position on the molding frame.

Referring to FIG. 2, the adjustable molding frame 10 is shown in the fully reclined position wherein the back panel 12 is oriented generally horizontally and the seat pan 14 is oriented generally vertically. With the adjustable molding frame thus positioned, the weight of a person positioned on the adjustable molding frame 10 will be substantially directed to and exerted upon a back vacuum bag (not shown in FIG. 2) positioned on the back panel 12. This orientation ensures that the surface contour formed in the back panel vacuum bag will accurately reflect the back contours of the person positioned upon the adjustable molding frame 10.

The adjustable molding frame 10 includes a molding frame tilt control assembly 50 mounted to the support frame 20 by means of support blocks 61A and 61B. In addition, the molding frame tilt control assembly 50 is pivotally mounted to a lower surface of the seat pan 14 by means of mounting blocks 58A and 58B. The molding frame tilt control assembly 50 includes pinions 52A and 52B positioned on a pinion shaft 53. The pinion shaft 53 has mounted on one end thereof a tilt control crank 51. Respective ends of the pinion shaft 53 are mounted to the support frame 20 by means of a mounting block 54 and a lock block 55. The pinion shaft 53 is free to rotate within the mounting and lock blocks 54, 55.

The molding frame tilt control assembly 50 further includes racks 57A and 57B coupled at a respective end thereof to a lower portion of the seat pan 14 by means of mounting blocks 58A and 58B, respectively. Each of the racks is free to pivot within a respective mounting block. The racks 57A and 57B respectively engage pinions 52A and 52B. With the racks 57A, 57B in abutting engagement with a respective pinion 52A, 52B, rotation of the pinion shaft 53 will cause the racks to be linearly displaced along the length thereof either upward or downward in unison so as to either raise or lower the seat pan 14. The seat pan 14 is mounted to the support frame 20 by means of a pivot bracket 59 through which is inserted a pivot pin 60 and about which the adjustable molding frame 10 pivots in response to rotation of the pinion shaft 53.

Figure 3:
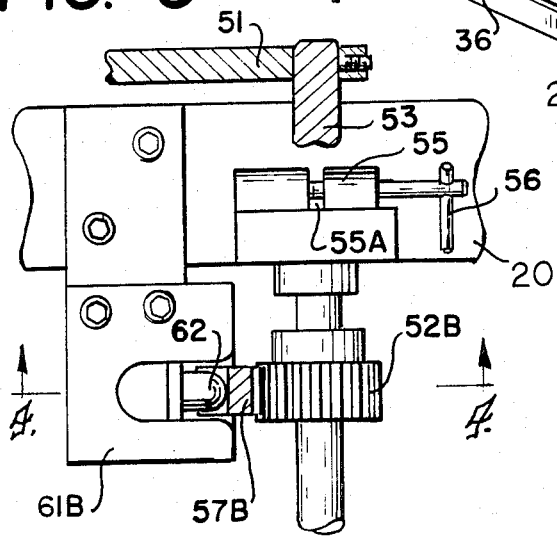
FIG. 3 is a sectional view taken along sight line 3—3 of FIG. 2 showing in detail a portion of the tilt control mechanism of the adjustable molding frame.
Figure 4:
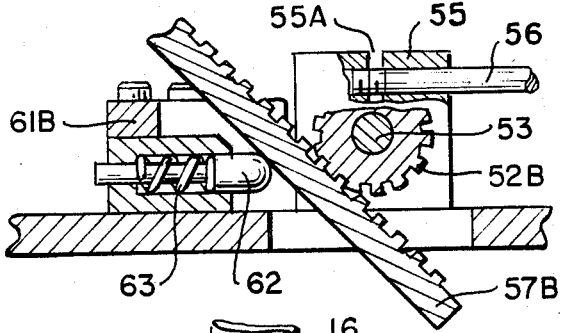
FIG. 4 is a sectional view taken along sight line 4—4 of FIG. 3 showing additional details of a portion of the tilt control mechanism of the adjustable molding frame.

Referring to FIGS. 3 and 4, the rack 57B is maintained in engagement with pinion 52B by means of an engaging pin 62. The engaging pin 62 is positioned within a rack support block 61B and is biased toward the pinion shaft 53 so as to engage and abut the flat surface of rack 57B by means of a spring 63. In response to the rotation of pinion 52B, the rack 57B is displaced along the length thereof either upward or downward in effecting the rotation of the adjustable molding frame 10 about pivot pin 60. As the seat pan 14 of the adjustable molding frame is displaced in response to the displacement of rack 57B, the rack itself will roll around the pitch line of pinion 52B so as to engage the pinion at different angular positions with respect to the pinion shaft 53. Engaging pin 62 provides for this relative movement of the rack 57B with respect to the pinion 52B in maintaining engagement between the grooved surfaces thereof. An arrangement similar to that just described is provided for maintaining rack 57A in contact with pinion 52A by means of an engaging pin (not shown) in the rack support block 61A.

Also shown in FIGS. 2, 3 and 4 is an arrangement for locking the adjustable molding frame 10 in position at a given tilt angle. This locking arrangement includes a threaded locking pin 56 inserted within the lock block 55 which includes a slot 55A therein. As the threaded locking pin 56 is tightened within the lock block 55, the facing, internal surfaces thereof immediately adjacent slot 55A are drawn together in exerting a compressive force around the circumference of the pinion shaft 53 in order to lock it in position. In this manner, the adjustable molding frame 10 may be securely positioned at virtually any tilt angle for as long as desired during the formation of contoured seating surfaces of a person supported thereon.

Also shown in FIG. 2 is a seat pan length control assembly 35 which has been actuated so as to fully extend the seat pan 14 outward from the back panel 12.

Figure 9:
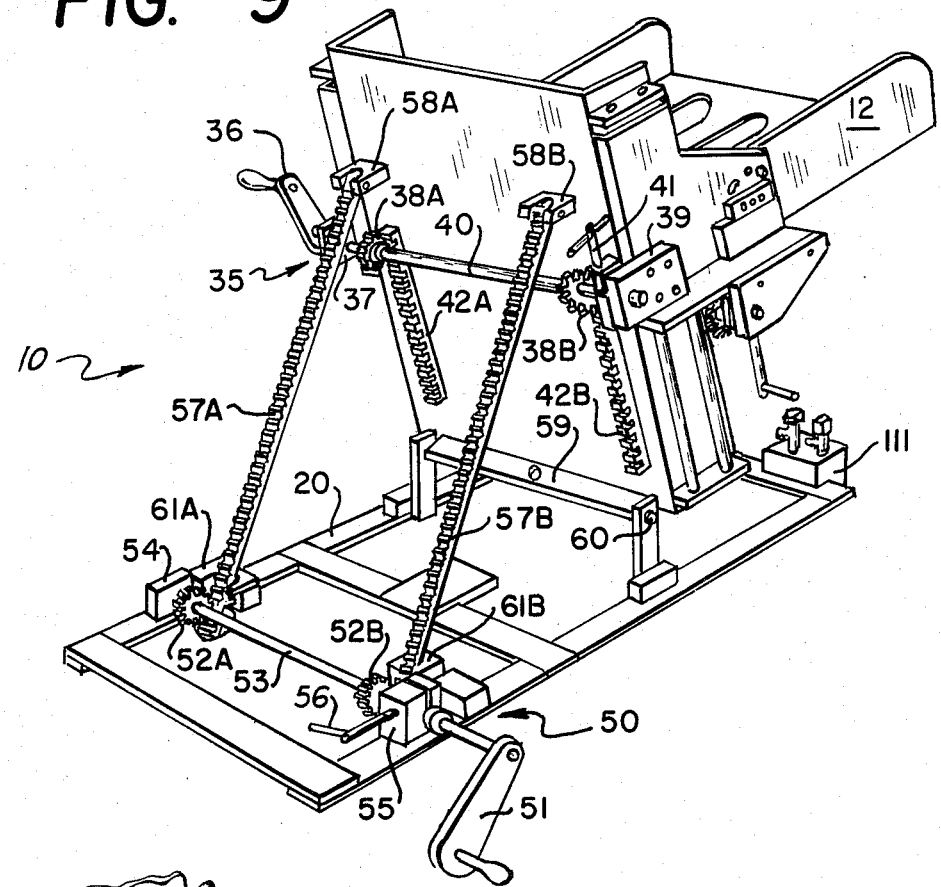
FIG. 9 is an upper perspective view of the adjustable molding frame in an inclined position showing the back panel in the full forward position with respect to the seat pan.

FIG. 9 also shows the adjustable molding frame 10 in a fully tilted position with the back panel 12 thereof in a generally horizontal orientation in which the back panel 12 is displaced by means of the seat pan length, or depth, control assembly 35 to the full forward position in providing the shortest seat pan length.

The seat pan length control assembly 35 includes pinions 38A and 38B mounted on a common pinion shaft 40. The pinion shaft 40 is coupled to the right and left L-shaped coupling brackets 16, 18 by means of a mounting block 37 and a lock block 39. With the pinion shaft 40 rotationally positioned within mounting block 37 and lock block 39, the pinion shaft 40 may be rotated by means of a crank handle 36 coupled to one end thereof. The pinions 38A and 38B respectively engage racks 42A and 42B securely mounted to a lower portion of the seat pan 14. When the pinion shaft 40 is rotated, the position of the seat pan 14 does not change, however, back panel 12 and right and left L-shaped brackets 16, 18 coupled thereto may be linearly displaced along the length of the seat pan 14 on the right and left guide bars 28, 30. Threadably inserted in lock block 39 is a locking pin 41 by means of which the pinion shaft 40 may be securely clamped within the lock block so as to preclude rotation of the pinion shaft and displacement of the back panel 12 along the seat pan 14. In this manner, the length of the seat pan 14 may be accurately adjusted and stably maintained in position while a person is supported upon the adjustable molding frame 10 and after he or she is removed therefrom during the process of making cushions contoured in accordance with the impressions made in the back and seat vacuum bags 22, 24.

Figure 5:
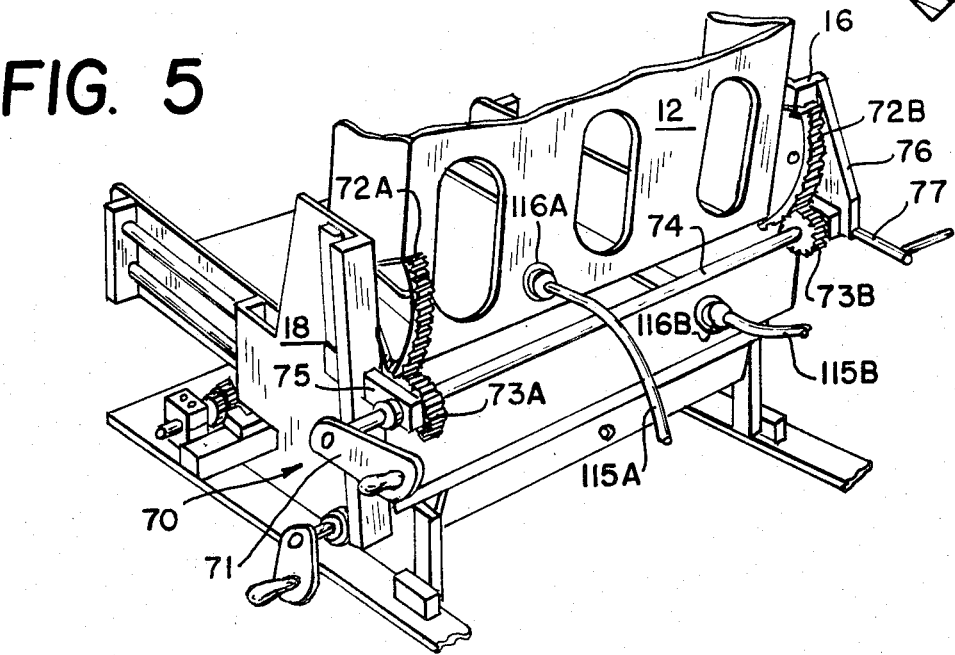
FIG. 5 is a perspective view showing details of the interconnection between the seat pan and back panel of the adjustable molding frame.
Figure 10:
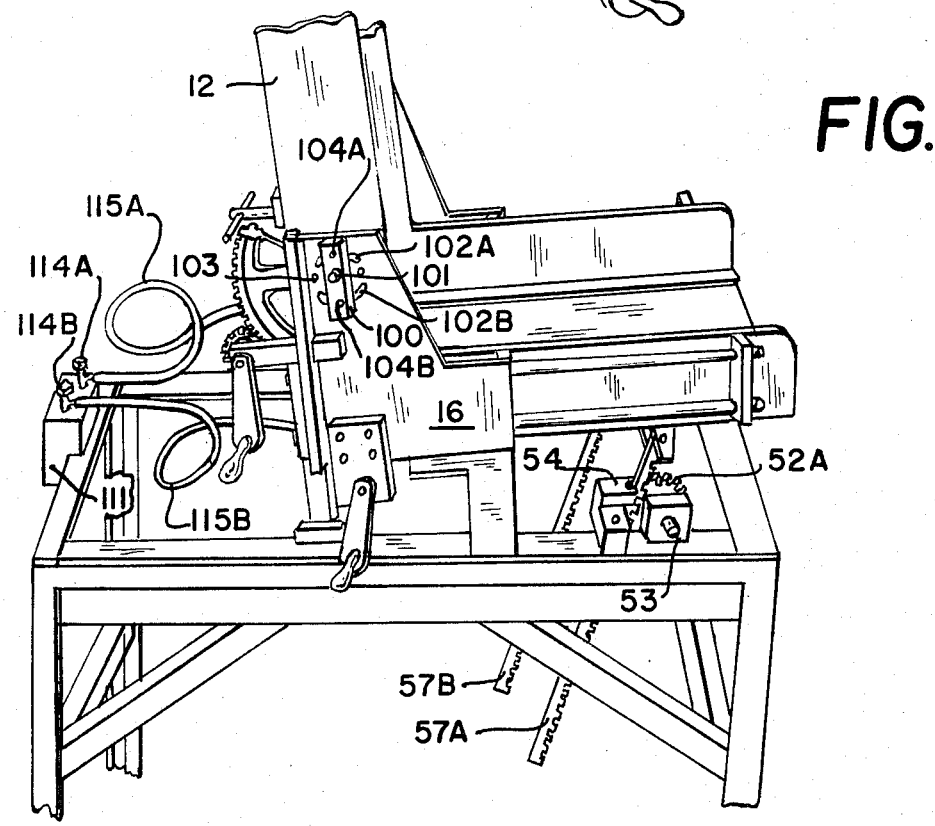
FIG. 10 is a perspective view showing various details of the adjustable molding frame of the present invention.
Figure 12:
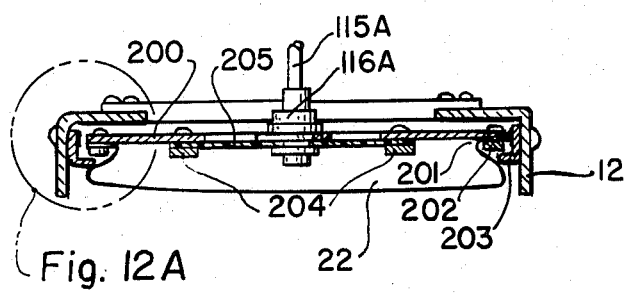
FIG. 12 is a sectional view of the back panel and vacuum bag combination of the adjustable molding frame of FIG. 1 taken along sight line 12—12 therein.
Figure 12A:
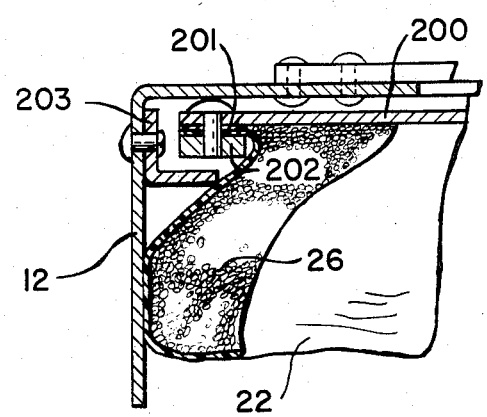
FIG. 12A is an enlarged view of a portion of FIG. 12 showing the details of the manner in which the back vacuum bag is positioned upon and mounted to the back panel.
Figure 13:
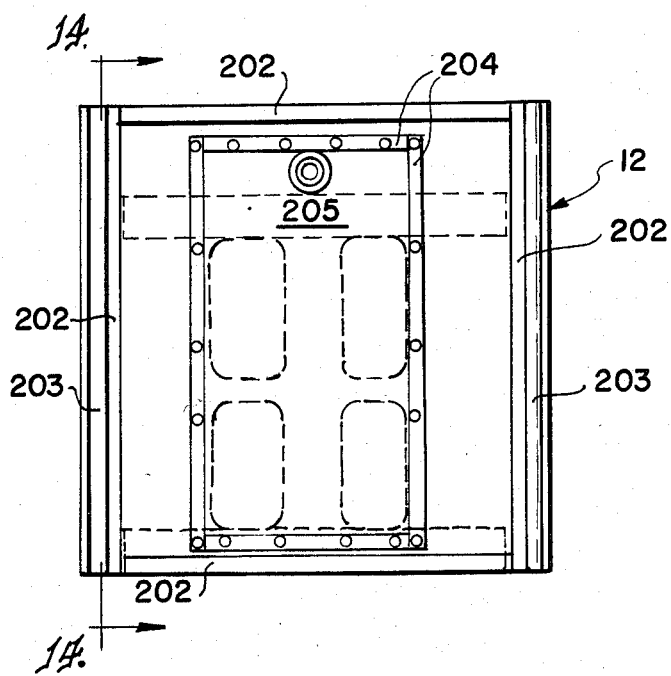
FIG. 13 is a front plan view of a back panel with the vacuum bag removed therefrom for use in the adjustable molding frame of the present invention.
Figure 14:
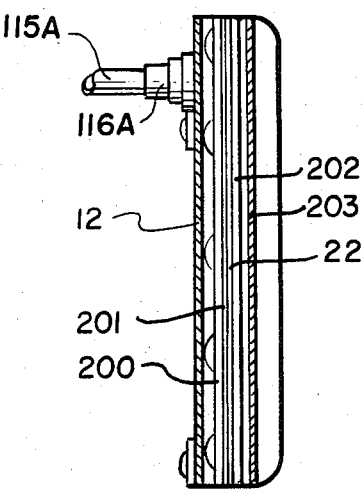
FIG. 14 is a sectional view of the back panel of FIG. 13 taken along sight line 14—14 therein.

Referring to FIGS. 5 and 10, there is shown a back tilt control assembly 70 for adjusting the seat-to-back angle in accordance with the dimensions and configuration of a person positioned upon the adjustable mounting frame 10. The back tilt control assembly 70 includes a pair of pinions 73A and 73B positioned upon a common pinion shaft 74 which is rotationally coupled to the right and left L-shaped brackets 16, 18 by means of a lock block 76 and a mounting bracket 75. Positioned on one end of the pinion shaft 74 is a back tilt control crank handle 71. Each of the pinions 73A, 73B engages a respective sector 72A, 72B, each of which includes a plurality of teeth therein. The sectors 72A, 72B are, in turn, fixedly coupled to the back panel 12. Rotation of pinion shaft 74 and pinions 73A, 73B thereon results in a corresponding rotation of sectors 72A, 72B and the back panel 12 coupled thereto. In this manner, the seat-to-back angle may be varied over a range of angular orientations and may be set as desired. The lock block 76 in which the pinion shaft 74 is mounted at one end thereof includes a threaded locking pin 77. By rotating the locking pin 77, the lock block 76 may be configured so as to engage the pinion shaft 74 in a clamping manner for securely and stably positioning the back panel 12 relative to the seat panel 14 at a predetermined angular orientation. This angular orientation may be roughly preset before the person is positioned upon the adjustable molding frame, precisely adjusted to conform with the person's posture and dimensions once positioned thereon, and remain in that configuration while the contoured cushions are being made.

Referring back to FIG. 1, it can be seen that a pair of foot supports are mounted to a forward, lower portion of the seat pan 14. Each of the foot supports 80A, 80B is coupled to the seat pan 14 by means of a respective adjustable positioning assembly 81A, 81B. FIG. 6 shows a partially cut away side view of the combination of a foot support 80A and an adjustable positioning assembly 81A. FIG. 7 is a sectional view taken along sight line 7—7 in FIG. 6 showing the details of the coupling between the foot support 80A and the adjustable positioning assembly 81A. Similarly, FIG. 8 is a sectional view taken along sight line 8—8 in FIG. 6 showing details of the coupling of the adjustable positioning assembly 81A to a lower portion of the seat pan 14. The configuration and operation of the combination of foot support 80A and adjustable positioning assembly 81A will now be explained with reference to FIGS. 6, 7 and 8, with the understanding that the following description applies equally as well to the combination of foot support 80B and adjustable positioning assembly 81B.

The adjustable positioning assembly 81A includes a forward pivoting linkage 84A pivotally coupled to the seat pan 14 by means of the combination of a forward mounting bracket 82 and a pivot pin 86. The adjustable positioning assembly 81A further includes an aft pivoting linkage 85 pivotally coupled to a lower portion of the seat pan 14 by means of the combination of an aft mounting bracket 83 and a pivot pin 87. Each of the forward and aft pivoting linkages 84, 85 include a plurality of teeth on an aft surface and along the length thereof. The aft pivoting linkage 85 is positioned within and along the length of a telescoping linkage 88. An aft portion of the telescoping linkage 88 includes an aperture 96 therein in which is inserted an upper adjustment bracket 89 which is pivotally coupled to the telescoping linkage 88 by means of a pivot pin 93. The upper adjustment bracket 89 includes an engaging projection 89A on a forward surface thereof for engaging in a complementary manner the teeth of a facing surface of the inner, aft pivoting linkage 85. The upper adjustment bracket 89 is maintained in engagement with the aft pivoting linkage 85 by means of a biasing spring 90. By grasping the upper adjustment bracket 89 so as to compress spring 90, the projection 89A on the upper adjustment bracket 89 may be disengaged from the aft pivoting linkage 85 to permit relative longitudinal displacement between the telescoping linkage 88 and the aft pivoting linkage 85.

The lower end portion of the telescoping linkage 88 is coupled to the footrest 80A by means of a pivot pin 95. Pivotally coupled to an aft portion of the foot support 80A by means of a pivot pin 94 is a lower adjustment bracket 91A. The lower adjustment bracket 91A includes an engaging projection 91B on a forward portion thereof for insertion between adjacent teeth of the facing surface of the forward pivoting linkage 84A. The lower adjustment bracket 91A is maintained in engagement with adjacent teeth in the forward pivoting linkage 84A by means of a biasing spring 92. By grasping the lower adjustment bracket 91A so as to compress the biasing spring 92, the lower adjustment bracket 91A may be disengaged from the forward pivoting linkage 84A which is then free to freely slide along the length thereof within an aft portion of the foot support 80A.

With the forward and aft pivoting linkages 84A, 85 pivotally coupled to the seat pan 14 and freely displaceable within the foot support 80A, the position of the foot support 80A may be continuously varied from a fully lowered position as shown in solid lines in FIG. 6 to a fully raised position as shown in dotted line form in FIG. 6. In order to raise the foot support 80A, it is displaced forward which will cause the forward and aft pivoting linkages 84A, 85 to pivot forward relative to the seat pan 14. Because of the displacement between the upper portions of the forward and aft pivoting linkages 84A, 85, as the foot support 80A is displaced forward and upward, the foot support 80A will move along the length of the forward pivoting linkage 84A toward the forward mounting bracket 82. As the foot support 80A is moved to its uppermost position, the lower adjustment bracket 91A will assume a position closest to the forward mounting bracket 82 along the length of the forward pivoting linkage 84A. While the foot support 80A is being pivotally displaced relative to the seat pan 14, the lower adjustment bracket 91 must be disengaged from the forward pivoting linkage 84A and the upper adjustment bracket 89 must be disengaged from the aft pivoting linkage 85. Once the foot support 80A is located in the desired position, the lower and upper adjustment brackets 91A, 89 may be released so as to respectively engage the forward and aft pivoting linkages 84A, 85. In this manner, the foot support 80A may be securely maintained in the desired position while ensuring the stable positioning of the feet and upper leg portions of a person supported upon the adjustable molding frame 10.

Figure 11:
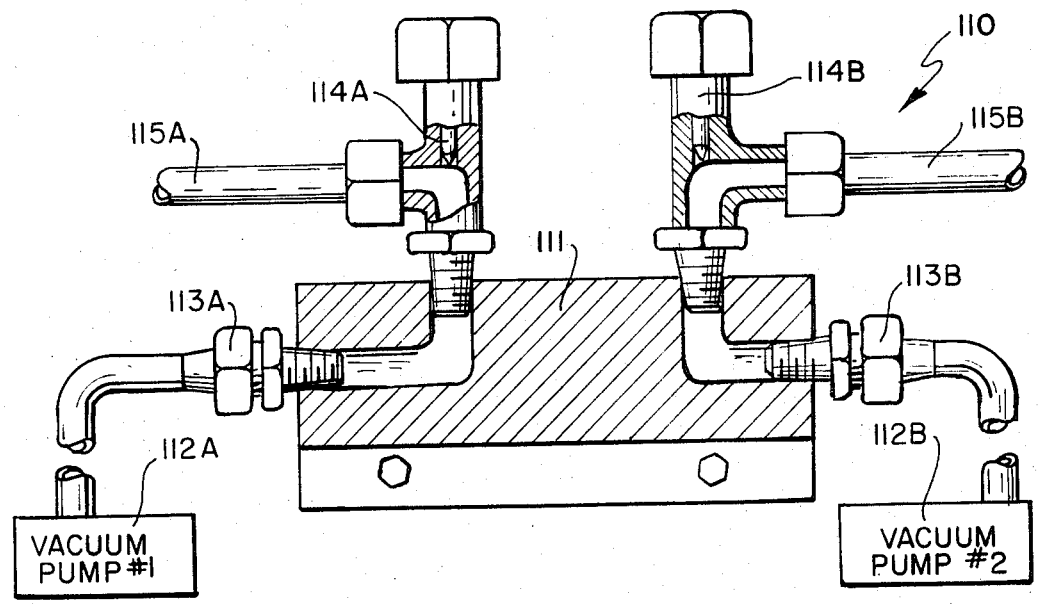
FIG. 11 is a sectional view of a vacuum system including a control manifold for use in the adjustable molding frame of the present invention.

Referring to FIG. 11, there is shown a simplified schematic diagram of a vacuum control system 110 for use in the adjustable molding frame of the present invention. The vacuum control system 110 includes a vacuum manifold 111 which may be mounted to an aft portion of the support frame 20 as shown in FIGS. 9 and 10. As shown in FIGS. 5 and 10, the vacuum manifold 111 is coupled to the back panel 12 and seat pan 14 by means of the respective combinations of a back panel fitting 116A and a first vacuum line 115A and a seat pan fitting 116B and a second vacuum line 115B. The back vacuum bag 22 is positioned upon the back panel 12 and is coupled to the back panel fitting 116A in a conventional manner to permit the vacuum bag to be evacuated by means of a vacuum pump. Similarly, the seat vacuum bag 24 is positioned upon the seat pan 14 and is coupled to the seat pan fitting 116B in a conventional manner to permit the vacuum bag to be evacuated by means of a vacuum pump coupled thereto.

As shown in FIG. 11, a first vacuum pump 112A is coupled to the vacuum manifold 111 by means of a fitting 113A. Similarly, a second vacuum pump 112B is coupled to the vacuum manifold 111 by means of a second fitting 113B. First and second control valves 114A, 114B respectively couple the vacuum manifold 111 to vacuum lines 115A, 115B which, in turn, lead respectively to the back panel 12 and to the seat pan 14. Control valves 114A and 114B are of the needle valve type and allow a respective vacuum pump to be coupled to a vacuum bag positioned on either the back panel 12 or the seat pan 14. In this manner, the back vacuum bag 22 may be evacuated first followed by evacuation of the seat vacuum bag 24, or vice versa, depending upon the procedure used for taking the seat support impressions of a person positioned upon the adjustable molding frame. In addition, the first and second control valves 114A, 114B permit the vacuum applied to a vacuum bag to be precisely controlled in order to permit preliminary manipulation of the support surfaces prior to a person being positioned upon the adjustable molding frame 10, followed by the application of a maximum vacuum applied thereto for providing a rigid surface configuration on a vacuum bag once an accurate contour impression has been made thereon.

Referring to FIGS. 12, 12A, 13 and 14, there will now be described the manner in which the back and seat vacuum bags 22, 24 are installed in and mounted to the back panel 12 and the seat pan 14, respectively. While the following description is directed specifically to the mounting and positioning of the back vacuum bag 22 upon the back panel 12, it is equally applicable to the mounting and positioning of the seat vacuum bag 24 upon the seat pan 14.

The back and seat vacuum bags 22, 24, which are preferably comprised of rubber or a rubber-like material, are easily installed within the back panel 12 and seat pan 14, respectively. Each of the back and seat vacuum bags 22, 24 is comprised of two separate sheets of rubber 22, 205. Both sheets of rubber 22, 205 are secured to a flat main mounting plate 200 which is inserted between the aft surface of the back panel 12 and a pair of rails 203 securely mounted to respective lateral portions of the back panel 12. The seat pan 14 is provided with a similar pair of guide rails for the positioning of a combination seat pan mounting plate and a pair of rubber sheets as described relative to the back panel 12. A vacuum fitting 116A is attached permanently to the main mounting plate 200 upon which the two separate sheets of rubber 22, 205 are attached.

One of the rubber sheets 205 is smaller than the other sheet of rubber 22 and is mounted to the center area of the main mounting plate 200 by means of a plurality of linearly arranged screws which pass through mounting holes in the rubber sheet 205 and matching holes through the main mounting plate 200. In addition, a plurality of nut plates 204 are provided with tapped holes on matching centers which are in alignment with the clearance holes on the main mounting plate 200 and the rubber sheet 205. It is in this manner that the smaller rubber sheet 205 is securely mounted to the main mounting plate 200, which may be slidably inserted within and along the length of the back panel 12.

The same general procedure as that described in the preceding paragraph is followed for installing the larger, outer sheet of rubber 22 with two exceptions. While the smaller rubber sheet 205 can be mounted flat upon the main mounting plate 200, the outer, larger rubber sheet 22 is best attached to the main mounting plate 200 by folding its four corners in a doubled manner which allows the outer rubber sheet 22 to remain an inch or so from the main mounting plate 200 in order to avoid stretching the rubber before sufficient platic beads 26 are positioned within the combination of the main mounting plate 200 and the two rubber sheets 22, 205. The finished bag will thus become a rectangular rubber cushion which lends itself to being distorted more easily, accurately, and reliably when the person being fitted sits on the molding frame because the thus formed rubber bag is evenly filled over its entire surface area. If the above outlined procedure is not followed, the curvilinear shape assumed by the rubber sheet 22 will not form in tight fitting relation around the person's individual configuration and curvature.

A gasket 201 is positioned between the outer, large rubber sheet 22 and the main mounting plate 200. Gasket 201 maintains the integrity of the vacuum seal between the main mounting plate 200 and the doubly folded edges of the large rubber sheet 22.

In assembling the combination of a vacuum bag and support shell, the gasket 201 is initially glued to the main mounting plate 200. Corresponding apertures in the gasket 201, the large rubber sheet 22, the nut plate 202, and the main mounting plate 200 are then positioned in alignment. Mounting bolts are then passed through the apertures of the four aforementioned components as previously described. Prior to installation of the last row of mounting bolts, the desired amount of plastic beads 26 are deposited into the finished bag assembly. When the final row of mounting bolts is secured, the finished bag assembly may be placed in the working position by sliding the assembly, which includes the combination of the rubber bag containing plastic beads attached to the main mounting plate 200, into the space between the back panel 12 and the pair of parallel guide rails 203. Attaching the combination of the vacuum coupling 116A and a vacuum hose 115A coupled thereto to the main mounting plate 200 completes the operation and the combination vacuum bag and back panel or seat pan is then ready for taking a seating impression of a person positioned upon the adjustable molding frame. The aforementioned configuration and procedure facilitates the replacement of a damaged bag and permits a vacuum bag/shell combination to be removed from the adjustable molding frame, while under vacuum, to permit another contoured seating surface individually configured to another person to be formed while a uniquely contoured cushion is being fabricated in accordance with the first person's seating surface impression.

There has thus been shown an adjustable molding frame having various degrees of freedom which allow it to be variably configured for obtaining surface impressions of the back and seat portions of an individual for the purpose of fabricating seat and back cushions uniquely contoured to that person. The flexibility of the adjustable molding frame of the present invention permits it to accommodate persons having a large range of bodily configurations, including severe deformities, in providing a seating surface contour impression which precisely images the unique configuration of the person positioned thereon.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

I claim:

1. Apparatus for providing a support surface uniquely contoured and configured to a person seated thereon, said apparatus comprising:
    a support structure;
    a seat pan positioned on said support structure;
    a back panel coupled to said seat pan;
    first and second pliable, sealed containers positioned respectively on said seat pan and said back panel;
    a deformable material located in said first and second sealed containers;
    first and second vacuum pumps coupled respectively to said first and second sealed containers for the evacuation thereof when a person is positioned thereon;

first control means coupling said seat pan and said back panel for adjusting the length of said seat pan in accordance with the dimensions of the person thereon;

second control means coupling said seat pan and said back panel for adjusting the angle therebetween in accordance with the orientation of the person thereon; and third control means coupling said support structure and said seat pan for rotating said apparatus rearward in orienting the back panel thereof generally horizontally with said person supported primarily thereon.

2. The apparatus of claim 1 wherein said deformable material comprises a plurality of closely packed beads freely displaceable with respect to one another.

3. The apparatus of claim 1 wherein each of said first and second sealed containers comprises a rubber bag including a fitting thereon for coupling said bag to a respective vacuum pump.

4. The apparatus of claim 3 wherein said fittings coupled to said first and second sealed containers are respectively mounted to said seat pan and to said back panel.

5. The apparatus of claim 1 further comprising a vacuum manifold coupling said first and second vacuum pumps to said first and second sealed containers, respectively.

6. The apparatus of claim 5 wherein said vacuum manifold includes first and second control means respectively coupled between said first vacuum pump and first sealed container and said second vacuum pump and second sealed container for independently controlling the evacuation of said sealed containers.

7. The apparatus of claim 6 wherein each of said first and second control means comprises a needle valve.

8. The apparatus of claim 1 wherein said first control means comprises a rack and pinion combination, with said rack mounted to a lower portion of said seat pan.

9. The apparatus of claim 8 further comprising locking means coupled to said rack and pinion combination for securing said seat pan in position relative to said back panel after said seat pan length has been adjusted as desired.

10. The apparatus of claim 1 wherein said second control means comprises a rack and pinion combination, wherein said rack is in the shape of a sector mounted to said back panel and said pinion is rotationally mounted to said seat pan.

11. The apparatus of claim 10 further comprising locking means coupled to said rack and pinion combination for securing said back panel at a predetermined angle relative to said set pan.

12. The apparatus of claim 1 wherein said third control means comprises a rack and pinion combination, with said pinion rotationally mounted to said support structure and a first end of said rack pivotally coupled to said seat pan.

13. The apparatus of claim 12 further comprising locking means coupled to said rack and pinion combination for securing said apparatus in a rearwardly inclined orientation.

14. The apparatus of claim 13 further comprising an engaging pin abutting said rack so as to displace said rack around a pitch line of said pinion in response to the rotation thereof.

15. The apparatus of claim 1 further comprising feet support means mounted to said seat pan for supporting the feet of said person and ensuring the proper positioning of said person's legs upon said first container.

16. The apparatus of claim 15 further comprising adjustable mounting means coupling said feet support means to said seat pan in permitting the position of said feet support means to be adjusted as desired.

17. The apparatus of claim 1 wherein said first and second sealed containers are slidably removable from said seat pan and said back panel, respectively.

18. The apparatus of claim 17 wherein said first and second sealed containers include respective mounting plates to which said deformable material is securely attached in a sealed manner and wherein said mounting plates are removable from said seat pan and said back panel.

* * * * *